(12) United States Patent
Diebold et al.

(10) Patent No.: US 7,904,166 B2
(45) Date of Patent: Mar. 8, 2011

(54) CONFIGURATION AND METHOD FOR THE MANAGEMENT OF DATA OF A PLURALITY OF PROGRAMMABLE PERSONAL MEDICAL DEVICES

(75) Inventors: Michael Diebold, Berlin (DE); Hans-Juergen Wildau, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 519 days.

(21) Appl. No.: 12/134,359

(22) Filed: Jun. 6, 2008

(65) Prior Publication Data

US 2009/0318998 A1 Dec. 24, 2009

(30) Foreign Application Priority Data

Jul. 19, 2007 (DE) .......................... 10 2007 033 992

(51) Int. Cl.
*A61N 1/08* (2006.01)
(52) U.S. Cl. ............................. 607/59; 607/31
(58) Field of Classification Search .................. None
See application file for complete search history.

(56) References Cited

U.S. PATENT DOCUMENTS

| 6,358,202 | B1 | 3/2002 | Arent |
| 6,418,346 | B1 * | 7/2002 | Nelson et al. ................... 607/59 |
| 2002/0040234 | A1 * | 4/2002 | Linberg ........................ 607/32 |
| 2005/0061336 | A1 | 3/2005 | Goetz et al. |
| 2005/0228693 | A1 | 10/2005 | Webb et al. |
| 2007/0136098 | A1 | 6/2007 | Smythe et al. |
| 2009/0018598 | A1 * | 1/2009 | Doerr et al. ..................... 607/30 |

FOREIGN PATENT DOCUMENTS

| DE | 60012368 | 12/2001 |
| DE | 10350538 | 6/2005 |
| WO | WO 2007/081829 | 7/2007 |

OTHER PUBLICATIONS

German Search Report, dated Jan. 29, 2008.

* cited by examiner

*Primary Examiner* — Kennedy J Schaetzle
(74) *Attorney, Agent, or Firm* — ARC IP Law, PC; Joseph J. Mayo

(57) ABSTRACT

The invention relates to a configuration and a method for the management of data of a plurality of programmable personal medical devices. The configuration comprises a first plurality of personal devices, a second plurality of patient devices each calibrated to at least one personal device, a third plurality of programming devices each calibrated to at least one personal device, a central management unit, a service center, and a management database. The patient devices and/or the programming devices are controlled using management data, upon establishment of the existence of a communication between the management unit and the patient device and/or a programming device, on the basis of this establishment and on the basis of stored management data, specific management data being transmitted to the patient device and/or programming device.

10 Claims, 3 Drawing Sheets

CONFIGURATION AND METHOD FOR THE MANAGEMENT OF DATA OF A PLURALITY OF PROGRAMMABLE PERSONAL MEDICAL DEVICES

This application takes priority from German Patent Application DE 10 2007 033 992.7, filed 19 Jul. 2007, the specification of which is hereby incorporated herein by reference.

BACKGROUND OF THE INVENTION

1. Field of the Invention

The invention relates to a configuration for the management of data of a plurality of programmable personal medical devices, in particular implantable medical devices, such as a cardiac pacemaker, defibrillator, or the like, having the following components: first plurality of personal devices, second plurality of patient devices, each calibrated to at least one personal device, third plurality of programming devices, each calibrated to at least one personal device, central management unit, service center, and management database.

2. Description of the Related Art

The management of data of a plurality of programmable personal medical devices essentially comprises two generally differentiable data streams in the present context.

On one hand, data in regard to the medical device and in regard to its operation occur during operation of a personal medical device such as a cardiac pacemaker or defibrillator. These data result on one hand from the operating state of the personal device itself and on the other hand from data which are detected by the personal device. Such data are significant in particular for optimum aftercare. Aftercare data which have been recorded by an implant are typically read out from the implant by a programming device and exchanged between the programming device and a hospital information system via local connections present in a hospital. A decentralized software installation is used in this case, which makes corresponding maintenance effort necessary. An object of the present invention is to provide a configuration and a method for the management of data such as aftercare data, by which maintenance effort is reduced in comparison to typical systems.

A further aspect results because, due to different specifications in particular hospital information systems, synchronization and/or central data collection for aftercare data in particular is only possible with great difficulties. It is conceivable that in addition to the particular local hospital information systems, there is a demand for providing national electronic patient files, for example. This may only be achieved with great difficulties in the event of a local data transfer as is typically provided.

BRIEF SUMMARY OF THE INVENTION

The object of the present invention is therefore also to provide a configuration for the management of data of personal medical devices which allows a central data management, for example, as national electronic patient files.

In the context of the present invention, the second data stream comprises particular altered and/or improved management data being provided in the course of a product improvements or product reworkings for different devices, which relate to the operation and the mode of operation of the particular devices themselves as the configuration, software, or firmware, for example. Updates of firmware are typically performed, for example, in that a suitable data carrier is physically input into the particular device to be updated. For example, a programming device is provided at its setup location with a CD which has an updated firmware version. A great logistical effort is thus necessary, which may also be subject to error. For example, if a data carrier having an update intended for a specific device is provided for another device, this update is typically rejected by the device, which makes renewed distribution of the data carrier necessary. In addition, because of the distribution of the data carrier, a time delay is unavoidable between the preparation and/or design of an update and the use of this update in the device. In addition, if multiple updates building on one another are provided, an update may be left out or the update chain may not be processed up to the end, because of which the particular device would not be at the intended update status.

A further object of the present invention is to provide a configuration and a method for the management of data, in which the problems described above are avoided during the supply of devices with management data such as upgrades or other updates.

The objects are achieved according to the invention by a configuration for the management of data of a plurality of programmable personal medical devices as defined in Claim 1. The objects are also achieved by a method for the management of data of a plurality of programmable personal medical devices as defined in Claim 10.

Advantageous embodiments of the invention are defined in particular in subclaims 2 through 9.

Further advantageous embodiments of the invention result by combination of features of the claims and from the following description of a preferred exemplary embodiment.

BRIEF DESCRIPTION OF THE DRAWINGS

The invention is explained in greater detail hereafter on the basis of a preferred exemplary embodiment with reference to the appended figures. In the figures.

DETAILED DESCRIPTION OF THE INVENTION

Figure 1:
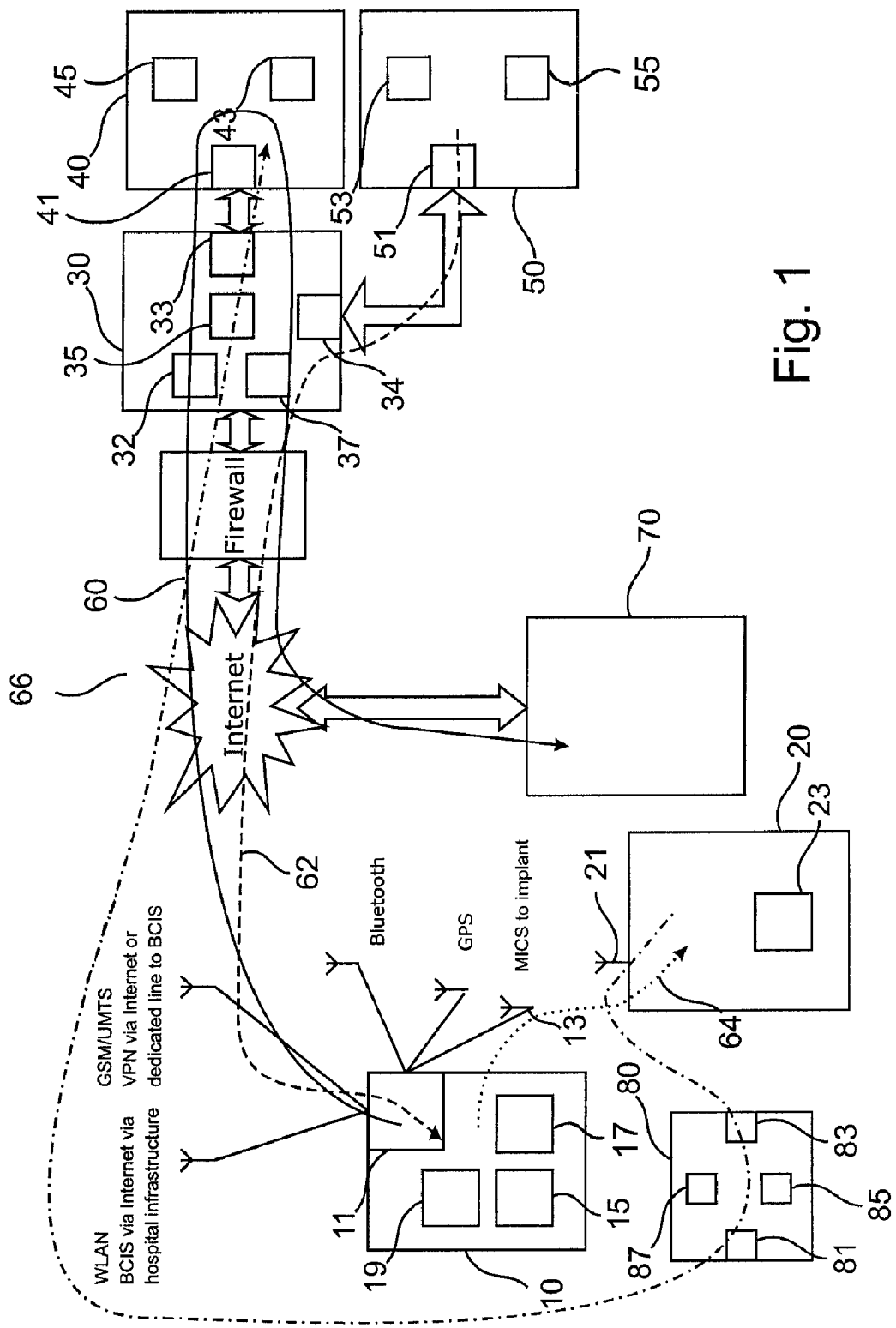
FIG. 1 shows a configuration according to the invention.

FIG. 1 shows a programming device 10 having a communication module 11, a memory unit 15, a configuration memory 17 and a programming unit 19, an implant 20 having a first interface 21, and a memory unit 23. In addition, a management unit 30 is provided with has a communication module 31 (see FIG. 2), a request unit 32, a first interface 33, a second interface 34, a management memory 35, an administration unit 36 (see FIG. 2), and a third interface 37. The management unit 30 is connected to a service center 40 in the form of a home monitoring service center (HMSC) via the first interface 33. The HMSC 40 has an interface 41, a memory unit 43, and a preparation unit 45. The management unit 30 is additionally connected via the second interface 34 to a management database 50, which has an interface 51 for communication with the management unit 30, a memory unit 53, and an administration unit 55.

The communication module 11 allows communication of the programming device 10 via a plurality of interfaces. The communication module 11 is, for a connection to the management unit, for example, connected via a WLAN terminal via the Internet and a hospital infrastructure or a GSM/UMTS contact, preferably by VPN via the Internet or a dedicated line, to the management unit. The communication module also has interfaces for Bluetooth communication or similar wireless technologies and an interface for a GPS system. The communication module is also equipped with an interface 13 for communication with the implant 20 per medical implant communication service specification.

FIG. 1 also shows a patient device 80 having a first interface 83, a request unit 85, a configuration memory 87, and a communication module 81. The communication module 81 corresponds to the communication module 11, although some details are not shown for the sake of clarity.

Moreover, the pathways of data flows are schematically shown in FIG. 1. The solid line 60 shows the pathway of aftercare data on the basis of data in regard to interactions of the programming device 10 with the implant 20. The aftercare data are provided by the memory unit 15 in a suitable way for communication and transmitted via the Internet and through a firewall to the management unit 30, which provides the data to the service center 40. Furthermore, the aftercare data are relayed via a suitable interface to a centralized electronic patient file 70.

In parallel to the aftercare data, the management unit 30 also receives configuration data, such as a firmware revision of the programming device and the implant. The corresponding data flow is not shown in FIG. 1 for the sake of clarity. On the basis of the configuration data, updates are provided for the programming device and the implant by the management database via the management unit 30. The pathway of the management data transmitted to the programming device for the update is indicated by the dashed line 62.

Together with the management data for the programming device 10, management data for the implant 20, such as a firmware update, are also transmitted. From the programming device 10, the management data provided for the implant 20 are transmitted to the implant 20 (dotted line 64). During the operation of the implant, data such as detected operating parameters are stored in the implant 20, which are transmitted from the implant 20 to the patient device 80. The request unit 85 of the patient device 80 is designed in the present case for the purpose of requesting data from the implant 20 via the first interface 83 of the patient device 80 on its own initiative. Moreover, the request unit 85 is also designed for the purpose of requesting data from the implant 20 upon prompting by the implant 20. In other words, this second type of request may also be referred to as a transmission of data from the implant 20 to the request unit 85. The requested implant messages are transmitted via the communication module 81 of the patient device 80 to the management unit 30. The management unit 30 transmits the implant messages to the home monitoring service center 40 (dot-dash line 66).

Figure 2:
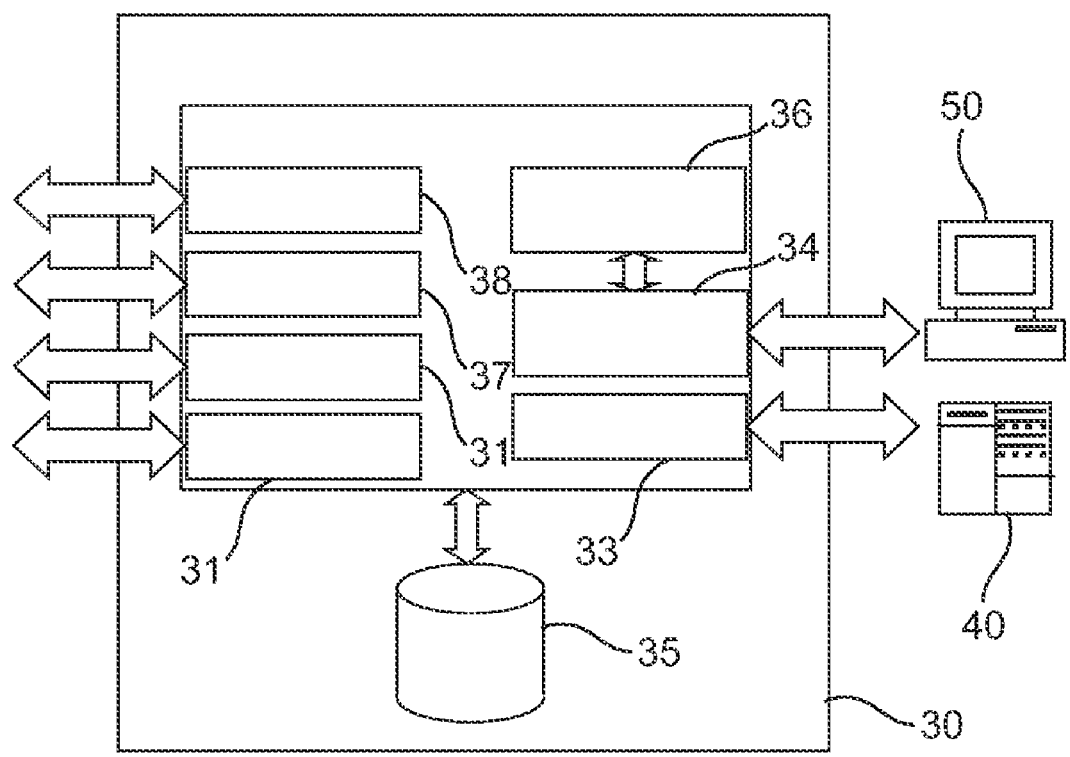
FIG. 2 shows a more detailed illustration of a partial aspect of the configuration from FIG. 1.

FIG. 2 shows a partial aspect of the configuration according to the invention shown in FIG. 1. The management unit 30 having a first and a second communication module 31 as the interface to a programming device and/or to a patient device is shown in FIG. 2. Furthermore, a first interface 33 for communication with a service center 40 and a second interface 34 for communication with a management database 50 are shown. The interface 34 is connected to an administration unit 36 for administering the management data which are stored in memory 35. In the present illustration, the management memory 35 assumes a part of the tasks which may be provided separately from the management unit in the management database 50 in an alternative embodiment.

Furthermore, the management unit is provided with a third interface 37, via which data requested by a request unit (not shown) may be transferred to an external patient database according to a predefined protocol.

Furthermore, the management unit 30 has an interface 38 which is used to maintain a special communication security. A security protocol such as the known RADIUS protocol is executed with the aid of the interface 38.

Figure 3:
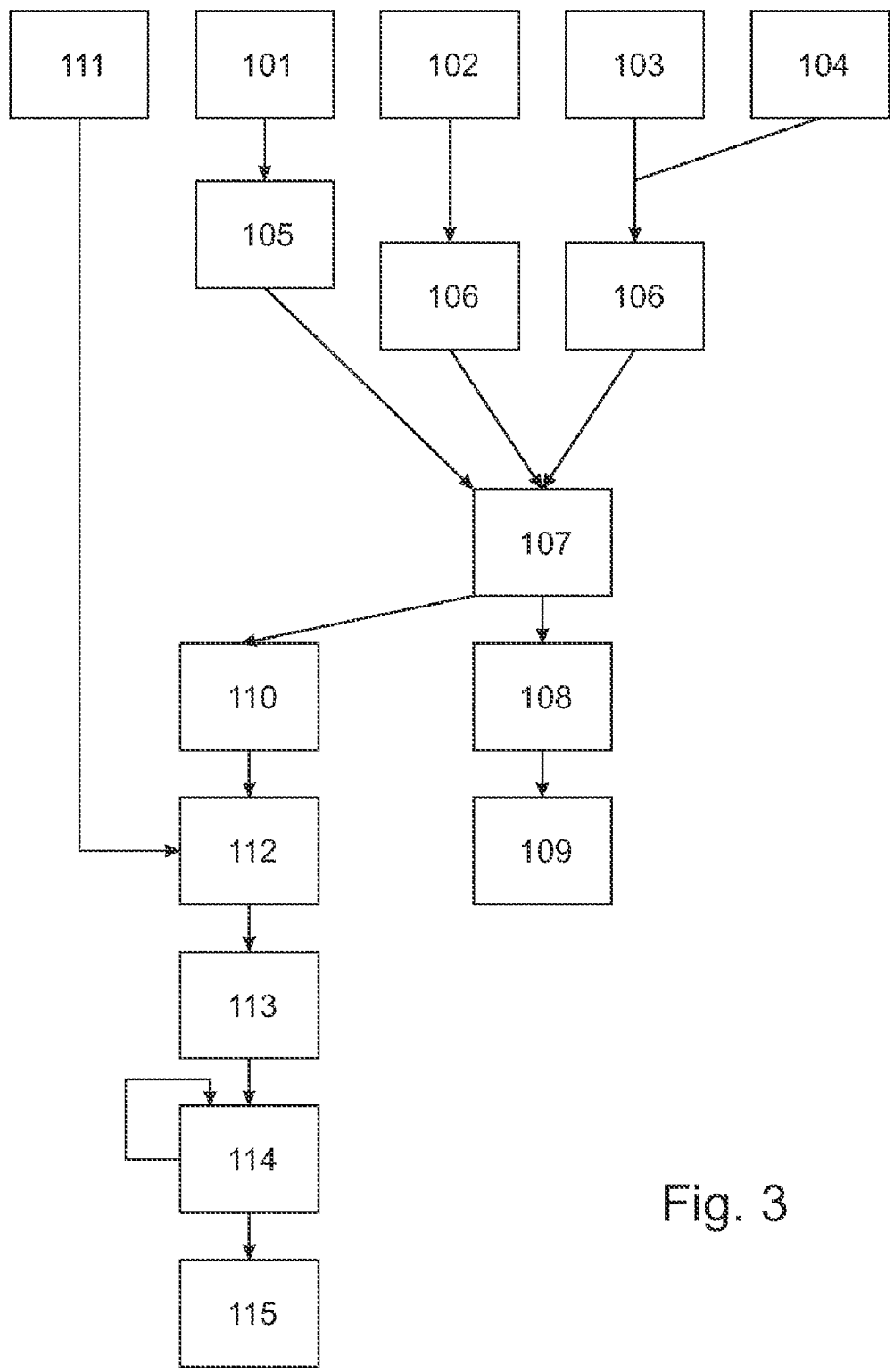
FIG. 3 shows a schematic sequence of the method according to the invention.

FIG. 3 schematically shows a sequence according to the invention of a method for the management of data of a plurality of programmable personal medical devices.

In step 101, data are stored in a memory unit of at least one personal device, these data relating in particular to operating parameters predefined for the device or detected by the device. In step 102, parallel configuration data for the configuration of at least one patient device are stored in a configuration memory of the particular patient device. In step 103, data in regard to interactions of at least one programming device are stored. In step 104, configuration data for the configuration of at least one programming device are also stored in a configuration memory of the particular programming device. In step 105, data stored in a memory unit of a personal device are requested by a request unit of a patient device calibrated to the personal device. In step 106, a secured, at least indirect communication between a communication module of a patient device and a programming device having a communication module of a management unit is established, followed in step 107 by a simultaneous or alternatively or supplementary sequential request of the request unit of a patient device, the configuration memory of a patient device, the memory unit of a programming device, and/or a configuration memory of a programming device by a request of the management unit. In step 108, the data requested in this case is relayed to a service center, which stores the received data in step 109 and prepares it for a predetermined display.

Data requested from the configuration memory of a patient device and/or a programming device are transmitted to a management database in step 110, in which previously in step 111 data for the management of the plurality of patient devices and/or the plurality of programming devices were stored in a memory unit. The management database provides data in step 112 for the management unit on the basis of the stored and transmitted data, which are stored in step 113 in a management memory of the management unit. This is followed in step 114 by a repeated check of the existence of a communication between the management unit and a patient device and/or a programming device, provided management data being transmitted to the patient device and/or to the programming device in step 115 on the basis of an establishment of an existing communication and on the basis of management data stored in the management memory.

In a working configuration, as provided according to the invention, the steps outlined as an example in FIG. 3 are executed partially in sequence and partially in parallel. Multiple method strands may also be executed in parallel according to the invention, however, if the particular special boundary conditions of the individual method steps did not preclude parallel processing of different sections of the method.

One embodiment of the invention is a central gateway server which supports the following functionalities:
  programming device fleet management
    prompt updating of the programming device software in the event of newly prepared software releases at the factory
    loading of software updates for network security at any time
    ensuring the software update process with retracing in the meaning of the medical product code (MPC) and similar international regulations automatic downloading of the new software from the central server automatic transmission of the location of the programming device by GPS or other location systems (e.g., A-GPS, based on radio and television transmitters, based on mobile wireless) for maintenance purposes automatic transmission of the software and hardware status and the next prescribed maintenance measures and times implant fleet management central acquisition of the firmware status of all implants location and time of the last request and/or reprogramming comparison of the stored data requested from the implant to expected values stored in the central database analysis of the data on the basis of statistically verified experiential values and warning of the physician in the event of significant deviations connection to electronic patient files/hospital information systems via standardized data protocols (e.g., HL7)

connection to hospital information systems connection to national and international, electronic patient/case files For example, the programming device is equipped with an internal or external communication module which produces a connection (VPN) to the common interface server (CIS) via a wireless, encrypted channel.

The following data, or at least a part thereof, are exchanged via this connection:

authentication data (access identification and password), using which the programming device authenticates itself at the CIS serial number of the programming device firmware revision(s) of the programming device and/or of components hardware revision(s) of the programming device and/or of components time of day configuration of the programming device serial number of the implants requested using the programming device configurations of the implants requested using the programming device firmware revision of the implants requested using the programming device data of the follow-ups performed using the programming device, if they have not yet been transmitted in a preceding session new firmware revision for the programming device new time of day new configuration of the programming device.

In addition to programming devices, patient devices according to the invention may also establish a link to the CIS. Instead of the follow-up data, they also transmit similar technical information such as:

medical and technical messages which the patient devices have received from the implants.

In an advantageous embodiment, the CIS accepts the follow-up and implant data from the programming and patient devices and relays them to the home monitoring service center for processing. A database-supported application is coupled to the CIS. All data which describe the configuration and statuses of the programming and patient devices are stored in this database. The coupled application provides functions, using which the programming and patient devices may be administered and updated. For example, a new firmware version may be provided on the CIS for individual devices, in groups, or for all devices, and downloaded thereto upon the next connection. Firmware updates for the implants are also contained in the new firmware of the programming device. The administration application has access to technical contents of the messages transmitted from the implants in addition to the data from the follow-ups. Thus, for example, it may be checked with the aid of the application whether and when new firmware versions were installed on the implants. To ensure the security and confidentiality of the stored data, the contents of the database are encrypted. These are thus secured against break-in or hacking. Programming and patient devices must authenticate themselves in relation to the CIS when the connection is established. It is thus ensured that only permitted devices may connect to the CIS. To achieve a connection to a standard network infrastructure, a RADIUS server is implemented in the CIS for the purpose of authentication. Hospital information systems and electronic patient or case files (clients) are connected to the CIS via standardized protocols. These are, for example, HL7 v2 or v3 via SSL/TCP/IP or ebXML. To ensure the confidentiality of the data, the clients must authenticate themselves with the CIS. This may be performed on one hand by an access identification and password or by a client certificate. The management application supports the administration of the access data and authorizations of the clients for this purpose.

In one embodiment, the invention relates to a processing unit having interface modules to:

programming device, patient device, mobile wireless networks (SMS connection, GPRS data connection, UMTS data connection) via virtual private network or dedicated line, Internet and local networks via Ethernet or WLAN, Home Monitoring Service Center, RADIUS clients, fleet management application (patient devices and programming devices), electronic patient/case files (electronic medical records) via HL7 v2 or v3 or similar, suitable standards via SSL+TCP/IP or ebXML, hospital information systems, and a processing unit having:

encryption module, administration application (programming devices, patient devices, accesses of the clients), RADIUS authentication module, data storage module, authorization module, and a database having:

authentication data of the programming and patient devices and the clients, serial numbers of the programming and patient devices, configuration of the programming and patient devices and the components, history of the configurations, installed firmware version, history of the installed firmware revisions, hardware IDs of all components, firmware ID, available firmware revisions, buffer for data which come from patient devices or programming devices, buffer for data which come from the home monitoring service center for delivery to patient and/or programming device, serial numbers of the implants requested using the programming device,
configurations of the implants requested using the programming device,
firmware revisions of the implants requested using the programming device,
data of the follow-ups performed using the programming device
and an application for administering the device classes programming device, patient device, and implant.

All requirements for the checking capability of the components in the meaning of the retracing ability according to MPC may be fulfilled by the central maintenance capability of the firmware statuses on the programming devices, patient devices, and the implants in the field. The encrypted connection provides a communication channel which is secure according to the current prior art, via which sensitive data such as programming device firmware, aftercare data, or implant messages may be transmitted. The central connection of the hospital information systems and case files permits a secure and rapid connection of the external client for the data exchange with the home monitoring system which is easy to administer.

What is claimed is:

1. A configuration for the management of data of a plurality of programmable personal medical devices, in particular implantable medical devices comprising a cardiac pacemaker, defibrillator, or the like having the following components:
   a first plurality of personal devices;
   a second plurality of patient devices each calibrated to at least one personal device;
   a third plurality of programming devices each calibrated to at least one personal device central management unit;
   a service center;
   a management database;
   said first plurality of personal devices each comprising
      a first interface for communication with at least one patient device calibrated to the at least one personal device and/or with at least one programming device calibrated to the at least one personal device;
      a memory unit for data, comprising operating parameters predefined for the at least one personal device and/or detected by the at least one personal device;
   said second plurality of patient devices each comprising
      a second interface for communication with the at least one personal device to which the particular patient device is calibrated;
      a request unit adapted to request data from the at least one personal device via the second interface;
      a configuration memory for data for configuration of the at least one patient device;
      a communication module for secured communication with the central management unit,
   said third plurality of programming devices each comprising
      a third interface for at least indirect communication with the at least one personal device to which the particular programming device is calibrated;
      a programming device communication module for secured communication with the central management unit;
      a memory unit for data in regard to interactions of the at least one programming device with the at least one personal device;
      a programming device configuration memory for data for configuration of the at least one programming device;
      a programming unit, which is implemented to compile a programming instruction for the at least one personal device on the basis of user input and transmit it to the at least one personal device via the third interface;
   said management unit comprising
      a management unit communication module for the secured communication with at least one patient device and/or at least one programming device;
      a request unit for the simultaneous and/or sequential requests of the request unit of a patient device, the configuration memory of a patient device, the memory unit of a programming device, and/or a configuration memory of a programming device;
      a fourth interface for communication with the service center;
      a fifth interface for communication with the management database;
      a management memory for management data;
      an administration unit adapted to administer the management data in the management memory;
   said service center comprising
      an sixth interface for communication with the management unit;
      a service center memory unit for data received from the request unit of the management unit;
      a preparation unit for preparing the data stored in the service center memory unit for a predetermined display;
   said management database comprising
      a seventh interface for communication with the management unit;
      a management database memory unit for data for management of the plurality of patient devices and/or the plurality of programming devices;
      a management database administration unit for providing data from the management database memory unit for the management unit on the basis of data received from the management unit from the configuration memory of at least one patient device and/or at least one programming device;
   wherein the patient devices and the programming devices are implemented to be controlled using management data, in particular freely programmable software, predetermined firmware, and/or on the basis of a predetermined parameter set; and,
   wherein the administration unit of the management unit is implemented to establish the existence of a communication between the management unit and a patient device and/or a programming device and, on the basis of this establishment and on the basis of management data stored in the management memory, to prompt a transmission of management data to the patient device and/or programming device.

2. The configuration according to claim 1, wherein the personal device is an active medical implant.

3. The configuration according to claim 2, wherein the personal device is an implantable cardiac pacemaker or defibrillator/cardioverter.

4. The configuration according to claim 1, wherein the administration unit is implemented for a continuous, regular, and/or individually activated establishment of a communication.

5. The configuration according to claim 1, wherein the management unit has another interface for the output of data requested by the request unit according to a predefined protocol, the protocol particularly being a HL7 v2 or HL7 v3 protocol and said another interface corresponding to a SSL/TCP/IP and/or an ebXML specification.

6. The configuration according to claim 1, wherein the administration unit of the management unit is implemented, for members of a group of programming devices and/or patient devices defined by a predetermined criterion, in the event of existence of a communication between the management unit and a particular device of the group, to prompt a transmission of management data provided for the group to the device, the group being able to comprise the entirety of the programming devices and/or the entirety of the patient devices.

7. The configuration according to claim 1, wherein the management unit and the service center are spatially separated from one another and may be coupled to one another via the particular interfaces.

8. The configuration according to claim 1, wherein the request unit of a patient device and/or the request unit may be prompted to a request by a prompt of the particular element to be requested.

9. The configuration according to claim 1, wherein the at least one personal device from the plurality of personal devices is implemented to be controlled using management data, in particular freely programmable software, predetermined firmware, and/or on the basis of a predetermined parameter set, the memory unit of the management database and the management memory being implemented to receive data for the management of the at least one personal device, and at least one programming device being implemented to receive management data for the at least one personal device from the management unit and relay it to the personal device.

10. A method for the management of data of a plurality of programmable personal medical devices, in particular implantable medical devices including a cardiac pacemaker, defibrillator, or the like, in particular using a configuration according to claim 1, having the following steps:

storing data in a memory unit of at least one personal device from a first plurality of personal devices, including operating parameters predefined by the particular personal device and/or detected by the particular personal device;

storing configuration data for the configuration of at least one patient device from a second plurality of patient devices in a configuration memory of the particular patient device;

storing data in regard to interactions of at least one programming device from a third plurality of programming devices with at least one personal device;

storing configuration data for the configuration of at least one programming device from the third plurality of programming devices in a configuration memory of the particular programming device;

requesting data stored in a memory unit of at least one personal device by a request unit of a patient device calibrated to the particular personal device;

establishing a secured, at least indirect communication between a communication module of at least one patient device and/or a programming device and a communication module of a management unit;

requesting, simultaneously and/or sequentially, of the request unit of a patient device, the configuration memory of a patient device, the memory unit of a programming device, and/or a configuration memory of a programming device by a request unit of the management unit;

transmitting the data requested by the request unit of the management unit to a service center;

storing data received from the request unit of the management unit in a memory unit of a service center and preparation of data stored in the memory unit of the service center for a predetermined display;

transmitting the data requested by the request unit of the management unit from the configuration memory of at least one patient device and/or at least one programming device to a management database;

storing data for the management of the plurality of patient devices and/or the plurality of programming devices in a memory unit of the management database;

providing of data from the memory unit for the management unit on the basis of data received by the management unit from the configuration memory of at least one patient device and/or at least one programming device;

storing of management data provided for the management unit in a management memory of the management unit;

controlling the patient devices and/or the programming devices using management data, in particular freely programmable software, predetermined firmware, and/or on the basis of a predetermined parameter set; and, transmitting management data to the patient device and/or programming device upon establishment of the existence of a communication between the management unit and a patient device and/or a programming device, on the basis of this establishment and on the basis of management data stored in the management memory.

* * * * *